(12) United States Patent
Pastrello et al.

(10) Patent No.: US 9,475,250 B2
(45) Date of Patent: Oct. 25, 2016

(54) METHOD FOR FOLDING INCONTINENCE PADS

(75) Inventors: Gabriele Pastrello, Milan (IT); Marco Rosani, Cremona (IT); Matteo Piantoni, Bergamo (IT); Luca Bugini, Bergamo (IT)

(73) Assignee: SCA HYGIENE PRODUCTS AB, Göteborg (SE)

(*) Notice: Subject to any disclaimer, the term of this patent is extended or adjusted under 35 U.S.C. 154(b) by 753 days.

(21) Appl. No.: 13/703,636

(22) PCT Filed: May 25, 2011

(86) PCT No.: PCT/IB2011/052279
§ 371 (c)(1),
(2), (4) Date: Feb. 4, 2013

(87) PCT Pub. No.: WO2011/158146
PCT Pub. Date: Dec. 22, 2011

(65) Prior Publication Data
US 2013/0130881 A1  May 23, 2013

(30) Foreign Application Priority Data

Jun. 15, 2010 (IT) .............................. BO2010A0378

(51) Int. Cl.
*A61F 13/15* (2006.01)
*B31F 1/00* (2006.01)
*A61F 13/551* (2006.01)

(52) U.S. Cl.
CPC ............. *B31F 1/0003* (2013.01); *A61F 13/15* (2013.01); *A61F 13/15747* (2013.01); *A61F 13/55135* (2013.01)

(58) Field of Classification Search
CPC ............ A61F 13/15; A61F 13/15365; A61F 2013/15121; A61F 13/15121; B31F 1/0003
USPC .......... 493/405, 379, 374, 381, 421; 604/385.02, 385.01, 385.201, 385.24
See application file for complete search history.

(56) References Cited

U.S. PATENT DOCUMENTS

| 4,701,177 A | * | 10/1987 | Ellis et al. | ................ 604/385.26 |
| 4,944,735 A | * | 7/1990 | Mokry | ..................... 604/385.26 |

(Continued)

FOREIGN PATENT DOCUMENTS

| CN | 1030520 A | 1/1989 |
| CN | 1368870 A | 9/2002 |

(Continued)

OTHER PUBLICATIONS

Chinese Office Action dated Dec. 3, 2014 issued in corresponding Chinese Patent Application No. 201180029355.8 and its English translation (11 pages).

(Continued)

*Primary Examiner* — Hemant M Desai
*Assistant Examiner* — Eduardo R Ferrero
(74) *Attorney, Agent, or Firm* — Drinker Biddle & Reath LLP

(57) ABSTRACT

A method including folding incontinence pads which have a substantially rectangular shape, elongate according to a longitudinal axis, and including a central absorbent pad and a perimetric edge. The method includes folding parts of the edge onto a central portion of the absorbent pad, folding a first end portion of the incontinence pad about a first fold line onto the central portion and a subsequent step of folding, about a second fold line a second end portion onto the first portion. The fold lines which are transversal to the longitudinal axis and define the central portion are spaced by a stretch which is greater than or equal to the longitudinal dimension of the first end portion. The folding step is preceded by a step of folding down inwards onto the central portion segments of the edge which lie between the first and second fold lines, and a step of retaining said segments of the edge on the central portion.

20 Claims, 2 Drawing Sheets

(56) References Cited

U.S. PATENT DOCUMENTS

| | | | |
|---|---|---|---|
| 5,281,209 A * | 1/1994 | Osborn et al. | 604/385.04 |
| 5,389,094 A * | 2/1995 | Lavash | A61F 13/472 |
| | | | 604/358 |
| H1639 H * | 3/1997 | Crainic | 604/368 |
| 5,681,303 A * | 10/1997 | Mills et al. | 604/385.26 |
| 5,752,946 A * | 5/1998 | Boberg et al. | 604/385.24 |
| 5,868,727 A * | 2/1999 | Barr et al. | 604/387 |
| 6,015,934 A | 1/2000 | Lee et al. | |
| 6,074,376 A * | 6/2000 | Mills | 604/390 |
| 6,168,582 B1 * | 1/2001 | Hasegawa | 604/385.02 |
| 6,312,417 B1 * | 11/2001 | Hansson | 604/385.02 |
| 6,312,418 B1 * | 11/2001 | Shimizu et al. | 604/385.02 |
| 6,371,948 B1 * | 4/2002 | Mizutani | A61F 13/47218 |
| | | | 156/227 |
| 6,497,692 B1 * | 12/2002 | Tameishi et al. | 604/385.02 |
| 6,502,695 B1 * | 1/2003 | Kim et al. | 206/440 |
| 6,511,464 B1 * | 1/2003 | Suekane | 604/385.04 |
| 6,517,525 B1 * | 2/2003 | Berthou et al. | 604/385.101 |
| 6,575,947 B1 * | 6/2003 | Tameishi et al. | 604/385.01 |
| 6,582,411 B1 * | 6/2003 | Carstens | A61F 13/15723 |
| | | | 604/358 |
| 6,802,833 B2 * | 10/2004 | Kudo | 604/385.02 |
| 6,902,552 B2 * | 6/2005 | VanGompel | A61F 13/4752 |
| | | | 604/385.04 |
| 7,427,277 B2 * | 9/2008 | Woltman et al. | 604/385.201 |
| 7,500,941 B2 * | 3/2009 | Coe et al. | 493/438 |
| 7,708,727 B2 * | 5/2010 | Woltman et al. | 604/385.201 |
| 7,908,824 B2 * | 3/2011 | Kuroda et al. | 53/416 |
| 8,211,074 B2 * | 7/2012 | Ohba et al. | 604/385.05 |
| 8,764,718 B2 * | 7/2014 | Hakansson et al. | 604/385.04 |
| 2004/0226843 A1 * | 11/2004 | Hermansson et al. | 206/440 |
| 2005/0234417 A1 * | 10/2005 | Yoshimasa et al. | 604/378 |
| 2005/0234418 A1 * | 10/2005 | Yoshimasa et al. | 604/378 |
| 2006/0264861 A1 * | 11/2006 | LaVon | A61F 13/49413 |
| | | | 604/385.201 |
| 2007/0250028 A1 * | 10/2007 | Woltman et al. | 604/385.02 |
| 2008/0132861 A1 * | 6/2008 | Tomes et al. | 604/367 |
| 2009/0292268 A1 * | 11/2009 | Bagger-Sjoback et al. | 604/385.01 |
| 2010/0036355 A1 * | 2/2010 | Hakansson et al. | 604/385.21 |
| 2010/0069870 A1 * | 3/2010 | Cohen | A61F 13/476 |
| | | | 604/385.04 |
| 2011/0046595 A1 * | 2/2011 | Drevik et al. | 604/385.02 |

FOREIGN PATENT DOCUMENTS

| | | |
|---|---|---|
| EP | 0 299 532 | 1/1989 |
| EP | 0 299 532 A2 | 1/1989 |
| EP | 0 749 742 A2 | 12/1996 |
| JP | H01-091862 | 11/1989 |
| JP | H09-000567 | 7/1997 |
| JP | H11-244329 A | 9/1999 |
| JP | 2010115368 A | 5/2010 |
| RU | 2192232 | 11/2002 |
| WO | 98/20823 | 5/1998 |
| WO | WO 98/25561 A1 | 6/1998 |
| WO | WO 99/23984 A1 | 5/1999 |

OTHER PUBLICATIONS

Japanese Office Action dated Mar. 2, 2015 issued in corresponding Japanese Patent Application No. 2013-514811 and its English translation (9 pages).

Examination Report pursuant to Article 94(3) EPC dated Jan. 15, 2014, issued in corresponding European Patent Application No. 11727297.1 (6 pages).

Chinese Office Action dated Apr. 2, 2014 issued in corresponding Chinese Patent Application No. 201180029355.8 and its English translation (10 pages).

Russian Decision on Grant issued in corresponding Russian patent application No. 2013101588 (and its English translation) (11 pages).

Mexican Office Action dated Oct. 26, 2015 issued in corresponding Mexican Patent Application No. MX/a/2012/014245 (5 pages) (with partial English translation 7 pages).

* cited by examiner

METHOD FOR FOLDING INCONTINENCE PADS

CROSS-REFERENCE TO PRIOR APPLICATION

This application is a §371 National Stage Application of PCT International Application No. PCT/IB2011/052279 filed on May 25, 2011, which claims priority to Italian Patent Application No. BO2010A000378 filed on Jun. 15, 2010, both of which are incorporated herein in their entirety.

TECHNICAL FIELD

This disclosure relates to a method for folding incontinence pads.

In particular, but without limiting the scope of the invention, this method can be applied for folding feminine light incontinence pads.

BACKGROUND

As is known, incontinence pads of the above-mentioned type have a substantially rectangular shape and include two sheets, one impermeable, the other absorbent, between which a section of padding is interposed, the padding made of absorbent material having a predetermined thickness.

At the outline of the incontinence pad, the two superposed sheets define a perimetric edge with a predetermined width.

The two longitudinal sides of the edge, at their central zone, have an elasticised segment.

As is known, machines for packaging incontinence pads of the above-mentioned type include a unit which folds them, about two fold lines which are transversal to their longitudinal axis, into three parts, respectively forming a front portion, a central portion and a rear portion of the incontinence pad.

Incontinence pads folded in this way into three superposed portions are then inserted individually or in groups in a wrapper by a further unit of the packaging machine.

It is also known that incontinence pads should have an anatomical shape.

That means that when the packaging of each incontinence pads is opened, the incontinence pads adopts a "V"- or "L"-shaped partly bent configuration, in which the front and rear portions, on the inner face side formed by the absorbent sheet, are facing each other in a position in which they are near and not coplanar, and in which the edges at only the elasticised central portion are folded towards each other, also on the side forming the inner face.

Said anatomical shape is difficult to obtain using the prior art folding units.

Consequently, at the moment of opening, the incontinence pad is substantially flat, or in any case is not positioned in an anatomically satisfactory way, but rather has unwanted fold lines.

SUMMARY

It is desired to provide a folding method which allows the obtainment of incontinence pads of the type described, which can adopt the above-mentioned anatomical shape after the folding operation and at the moment they are used.

It is also desired to provide a folding method according to which the folded incontinence pads have an optimum reduction in their dimensions.

BRIEF DESCRIPTION OF THE DRAWINGS

Further features and advantages of embodiments of the invention are more apparent in the description which follows of a preferred non-limiting embodiment of a method for folding incontinence pads, illustrated in the accompanying drawings, in which.

DETAILED DESCRIPTION OF PREFERRED EMBODIMENTS

Figure 1:
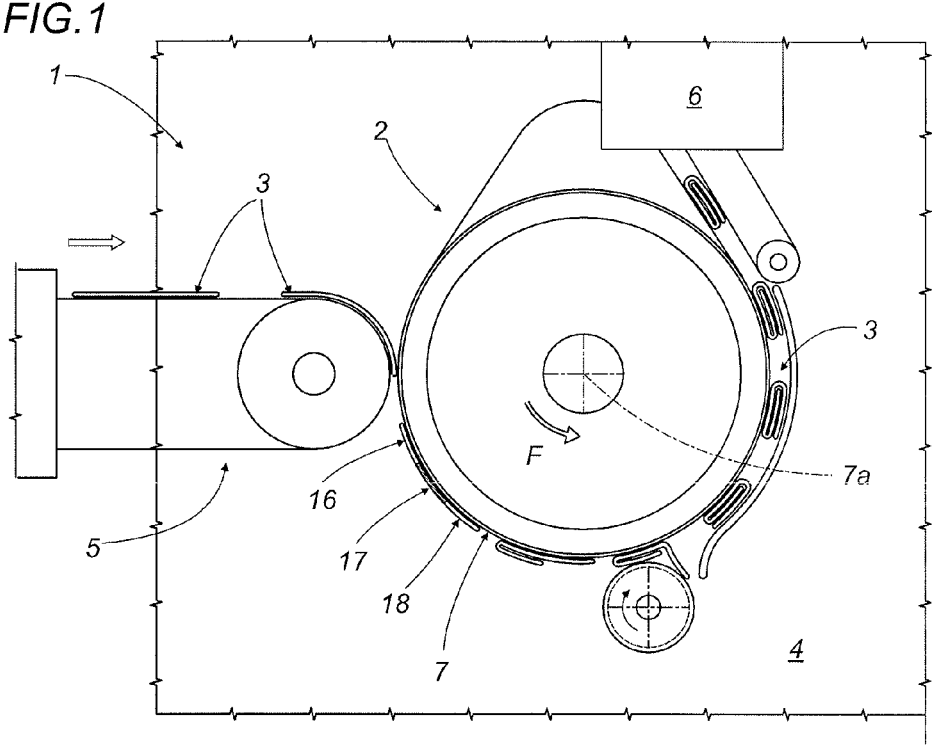
FIG. 1 is a schematic front view of a unit for folding incontinence pads for implementing the method according to an embodiment of the invention.
Figure 2:
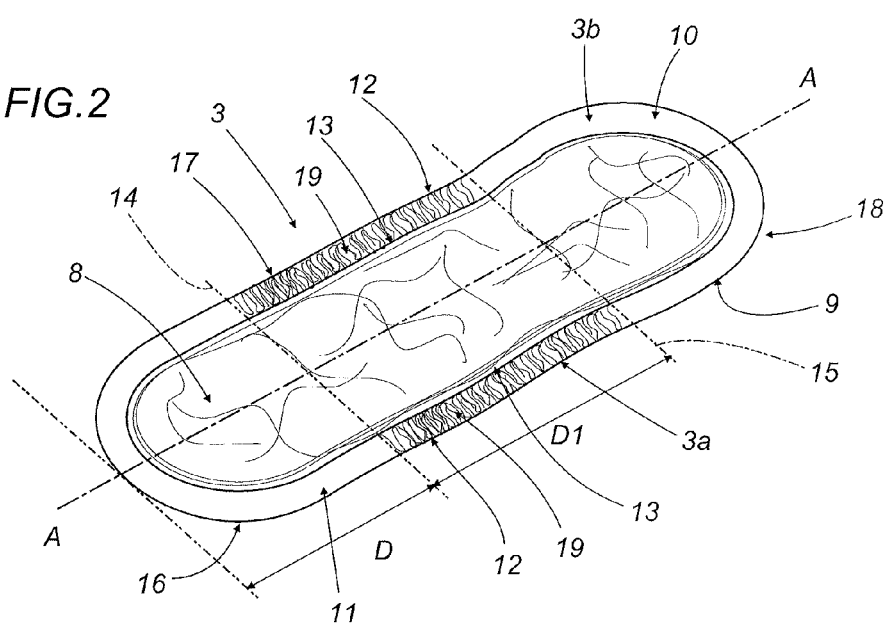
FIG. 2 is a perspective view of an incontinence pad processed by the unit of FIG. 1.

With reference to FIGS. 1 and 2, the numeral 1 denotes, by way of example only to allow a better interpretation of the folding method described below, a machine for packaging incontinence pads, including a unit 2 for folding incontinence pads 3, supported by a vertical wall 4.

The packaging machine 1 includes a feed unit 5 and a user unit, schematically illustrated as a block 6, interposed between which there is the folding unit 2 operating on the incontinence pads 3 during their transfer by conveyor means which for example consist of a drum 7.

The drum 7 rotates continuously anti-clockwise in the direction indicated by the arrow F about an axis 7a which is at a right angle to the wall 4.

Also with reference to FIG. 2, the incontinence pads 3 have a substantially rectangular shape, elongate according to a longitudinal axis A and include a section of padding or absorbent pad 8 which is closed between a sheet 9 of impermeable material (for example, polyethylene) which forms the outer face, labelled 3a, of the incontinence pad 3, and a sheet 10 of permeable material (for example non-woven material) which forms the inner face, labelled 3b, of the incontinence pad 3.

Along the outline of the incontinence pad 3 the two sheets 9 and 10 are sealed directly to each other, in such a way as to form around the absorbent pad 8 a perimetric edge 11 with predetermined width.

The numeral 12 denotes the two longitudinal segments of the edge 11 extending from the respective sides, labelled 13, of the absorbent pad 8.

The incontinence pads 3, angled with the axis A transversal to the axis 7a, are therefore transferred by the drum 7 in the direction indicated by the arrow F.

As will be illustrated below, the method includes a step of folding the incontinence pad 3, about fold lines 14 and 15 transversal to the axis A, into three portions, hereinafter referred to respectively as the rear portion or first end portion 16, the central portion 17 and the front portion or second end portion 18 of the incontinence pad 3.

It should be noticed that the term "central portion 17" refers to an intermediate portion of the incontinence pad 3, substantially cantered, but not necessarily precisely centred, between the end portions 16 and 18.

The two longitudinal segments 12 of the perimetric edge 11, at least at the central portion 17, include an elasticised part 19.

The presence of the elasticised parts 19 means that, when the packaging is opened, the rear portion 16 of the incontinence pad 3 adopts a predetermined angle relative to the central portion 17, such that it gives the incontinence pad 3 an anatomical shape.

Figure 3:
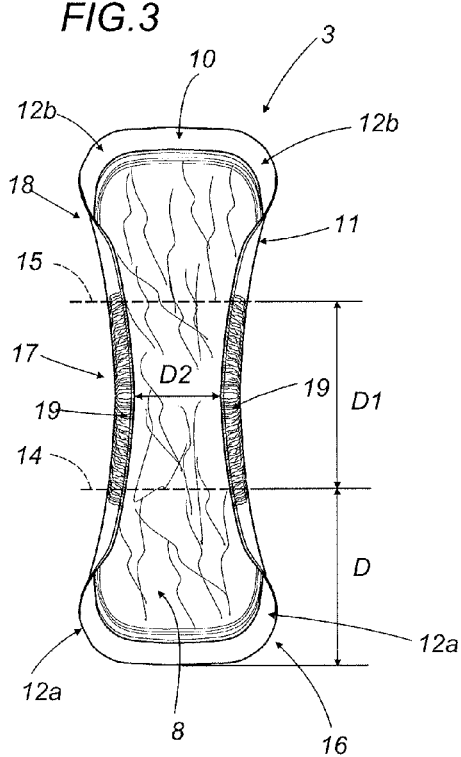
FIGS. 3, 4, 5, and 6 are perspective views of successive steps of folding the incontinence pad of FIG. 1.

As illustrated in FIG. 3, a first step of the folding method includes folding the elasticised parts 19 of the two longitudinal segments 12 of the edge 11 until they are in contact with the central portion 17.

In that condition the transversal dimension, labelled D2, of the incontinence pad 3, at the intermediate position of the central portion 17 and between the two folded elasticised parts 19, is preferably between 35 and 70 mm.

The first step, which gives the incontinence pad 3 a substantially hourglass shape, is followed by a step of securing the elasticised parts 19 which were folded down inwards.

Figure 4:
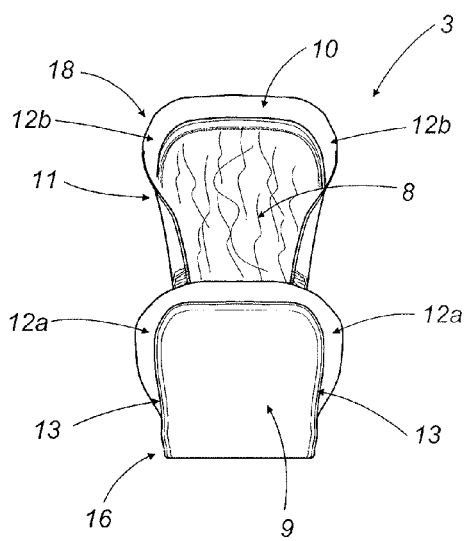

Said securing step continues at least until a first sub-step, illustrated in FIG. 4, of the step of folding the incontinence pad 3 about the fold lines 14 and 15.

During said sub-step the portion 16, which, for example, in use forms the rear portion of the incontinence pad 3, is folded about the fold line 14 until it is in contact with the central portion 17.

Figure 5:
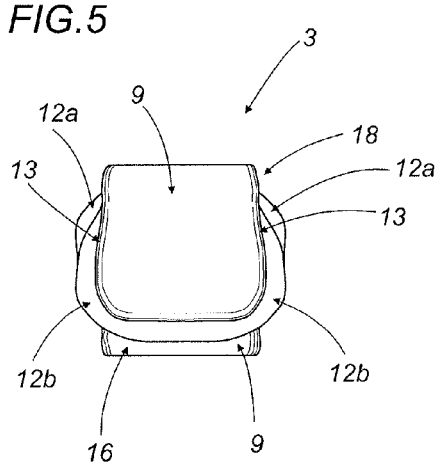

Then, in a further sub-step, illustrated in FIG. 5, of the same folding step, the portion 18, which, for example, in use forms the front portion of the incontinence pad 3, is folded about the fold line 15 until it is in contact with the portion 16, already folded.

It should be noticed that there is no difference if the front portion becomes the portion labelled 16 and, consequently, the rear portion becomes the one labelled 18.

The fold line 15 about which the front portion 18 rotates is separated from the fold line 14 by a stretch equal to or greater than the longitudinal dimension, labelled D, of the rear portion 16.

The distance between the fold lines 14 and 15, labelled D1, is preferably between 60 and 150 mm and is at least equal to one third of the longitudinal dimension of the incontinence pad 3. In other words, D1 may be equal to or greater than one third of the length of the incontinence pad 3.

That prevents folding of the front portion 18 from causing an unwanted folding of an end stretch of the rear portion 16.

It should be noticed that, after the two elasticised parts 19 have been folded down inwards onto the central portion 17, the two ends of the longitudinal segments 12, respectively labelled 12a and 12b, extend, in a wing-like fashion, respectively from the two portions 16 and 18.

After the sub-step of folding the front portion 18 towards the central portion 17 until it is superposed on the portion 16 which was previously folded into contact with the central portion 17, the ends or wings 12a and 12b are superposed.

Figure 6:
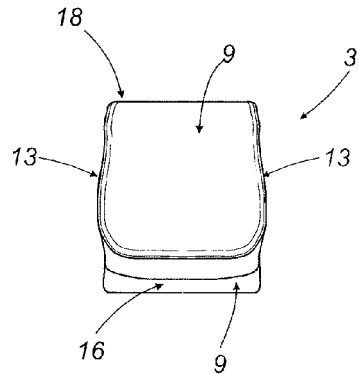

As illustrated in FIG. 6, a subsequent and final folding step includes folding down inwards the wings 12a and 12b of the first end portion 16 and of the second end portion 18 about the portion 16 towards the respective sides of the central portion 17 of the incontinence pad 3, preferably until they make contact with the sides 13 of the absorbent pad 8.

That produces precise folding of the incontinence pad 3, which, unlike what happens with the prior art methods, adopts its minimum overall dimensions and can be subjected to subsequent wrapping operations, either individually or in groups, by the user unit 6, without the creation of unwanted folds and deformations.

The invention claimed is:

1. A method for folding incontinence pads having a substantially rectangular shape, elongate and having a first end portion, central portion, and second end portion according to a longitudinal axis, and comprising a central absorbent pad, a back sheet, a top sheet, and a perimetric edge comprising perimetric edges of the back sheet and the top sheet, the method comprising, in the following order, steps of:
    folding elasticized segments of the perimetric edge located on sides of the incontinence pads opposed across the longitudinal axis down inwards onto the top sheet in the central portion;
    retaining the elasticized folded segments on the top sheet in the central portion; and
    folding each incontinence pad at a first and a second fold line both transversal to the longitudinal axis, the folding step comprising a first sub-step of folding the first end portion of the incontinence pad about the first fold line onto the top sheet in the central portion of the incontinence pad, and a second sub-step of folding the second end portion of the incontinence pad about the second fold line onto the first end portion,
    wherein the distance between the first and second fold lines measured along the longitudinal axis of the incontinence pad is greater than or equal to the longitudinal dimension of the first end portion, and
    wherein the elasticized folded segments are located between the first and second fold lines, and,
    wherein, before being folded, the elasticized segments extend away from the central absorbent pad in the transverse direction no further than an extent in the transverse direction of non-elasticized segments of the perimetric edge along the same side of the central absorbent pad.

2. The method according to claim 1, wherein the retaining step continues at least until the end of the first folding sub-step.

3. The method according to claim 1, wherein the distance between the first and second fold lines is equal at least to one third of the longitudinal dimension of the entire incontinence pad.

4. The method according to claim 3, wherein the distance between the first and second fold lines is between 60 and 150 mm.

5. The method according to claim 1, wherein, once folded down inwards onto the top sheet in the central portion, the elasticized folded segments are separated from each another in a direction at a right angle to the longitudinal axis of the incontinence pad by a distance of between 35 and 70 mm.

6. The method according to claim 1, wherein the first end portion of the incontinence pad constitutes, in use, the front portion of the incontinence pad.

7. The method according to claim 1, wherein the first end portion of the incontinence pad constitutes, in use, the rear portion of the incontinence pad.

8. The method according to claim 1, wherein the second folding sub-step is followed by a step of folding the non-elasticized segments of the perimetric edge between the first fold line and a first end of the incontinence pad and the non-elasticized segments of the perimetric edge between the second fold line and a second end of the incontinence pad around the first end portion and towards sides of the central portion of the central absorbent pad.

9. The method according to claim 1, wherein the second folding sub-step is followed by a step of folding the non-elasticized segments of the perimetric edge between the first fold line and a first end of the incontinence pad and the non-elasticized segments of the perimetric edge between the second fold line and a second end of the incontinence pad around the first end portion until they are superposed on sides of the central portion of the central absorbent pad.

10. The method of claim 1, wherein the elasticized segments are adapted to cause the first end portion to adopt a predetermined angle relative to the central portion.

11. A method for folding incontinence pads having a substantially rectangular shape, elongate and having a first end portion, central portion, and second end portion according to a longitudinal axis, and comprising a central absorbent pad, a back sheet, a top sheet, and a perimetric edge comprising perimetric edges of the back sheet and the top sheet, the method comprising, in the following order, steps of:

folding elasticized segments of the perimetric edge located on sides of the incontinence pads opposed across the longitudinal axis down inwards onto the top sheet in the central portion, wherein non-elasticized segments of the perimetric edge remain unfolded during this folding step;

retaining the elasticized folded segments on the top sheet in the central portion;

folding each incontinence pad at a first and a second fold line both transversal to the longitudinal axis, the folding step comprising a first sub-step of folding the first end portion of the incontinence pad about the first fold line onto the top sheet in the central portion of the incontinence pad, and a second sub-step of folding the second end portion of the incontinence pad about the second fold line onto the first end portion; and folding some of the non-elasticized segments of the perimetric edge towards the central absorbent pad, wherein the distance between the first and second fold lines measured along the longitudinal axis of the incontinence pad is greater than or equal to the longitudinal dimension of the first end portion, and wherein the elasticized folded segments are located between the first and second fold lines, and wherein, before being folded, the elasticized segments extend away from the central absorbent pad in the transverse direction no further than an extent in the transverse direction of non-elasticized segments of the perimetric edge along the same side of the central absorbent pad.

12. The method according to claim 11, wherein the retaining step continues at least until the end of the first folding sub-step.

13. The method according to claim 11, wherein the distance between the first and second fold lines is equal at least to one third of the longitudinal dimension of the entire incontinence pad.

14. The method according to claim 11, wherein the step of some of the non-elasticized segments includes folding the non-elasticated segments of the perimetric edge between the first fold line and a first end of the incontinence pad and the non-elasticated segments of the perimetric edge between the second fold line and a second end of the incontinence pad around the first end portion and towards sides of the central portion of the central absorbent pad.

15. The method according to claim 11, wherein the step of some of the non-elasticized segments includes folding the non-elasticized segments of the perimetric edge between the first fold line and a first end of the incontinence pad and the non-elasticized segments of the perimetric edge between the second fold line and a second end of the incontinence pad around the first end portion until they are superposed on sides of the central portion of the central absorbent pad.

16. A method for folding incontinence pads having a substantially rectangular shape, elongate and having a first end portion, central portion, and second end portion according to a longitudinal axis, and comprising a central absorbent pad, a back sheet, a top sheet, and a perimetric edge comprising perimetric edges of the back sheet and the top sheet, wherein the perimetric edge has substantially the same width around the entire periphery of the central absorbent pad, the method comprising, in the following order, steps of:

folding elasticized segments of the perimetric edge located on sides of the incontinence pads opposed across the longitudinal axis down inwards onto the top sheet in the central portion;

retaining the elasticized folded segments on the top sheet in the central portion; and folding each incontinence pad at a first and a second fold line both transversal to the longitudinal axis, the folding step comprising a first sub-step of folding the first end portion of the incontinence pad about the first fold line onto the top sheet in the central portion of the incontinence pad, and a second sub-step of folding the second end portion of the incontinence pad about the second fold line onto the first end portion, wherein the distance between the first and second fold lines measured along the longitudinal axis of the incontinence pad is greater than or equal to the longitudinal dimension of the first end portion, and wherein the elasticized folded segments are located between the first and second fold lines.

17. The method according to claim 16, wherein the retaining step continues at least until the end of the first folding sub-step.

18. The method according to claim 16, wherein the distance between the first and second fold lines is equal at least to one third of the longitudinal dimension of the entire incontinence pad.

19. The method according to claim 16, wherein the second folding sub-step is followed by a step of folding segments of the perimetric edge between the first fold line and a first end of the incontinence pad and segments of the perimetric edge between the second fold line and a second end of the incontinence pad around the first end portion and towards sides of the central portion of the central absorbent pad.

20. The method according to claim 16, wherein the second folding sub-step is followed by a step of folding segments of the perimetric edge between the first fold line and a first end of the incontinence pad and segments of the perimetric edge between the second fold line and a second end of the incontinence pad around the first end portion until they are superposed on sides of the central portion of the central absorbent pad.

\* \* \* \* \*